(12) United States Patent
Putz (10) Patent No.: US 6,671,534 B2
(45) Date of Patent: Dec. 30, 2003

(54) ELECTRICAL CONNECTOR FOR MULTI-CONTACT MEDICAL ELECTRODES

(75) Inventor: David A. Putz, Franksville, WI (US)

(73) Assignee: Ad-Tech Medical Instrument Corporation, Racine, WI (US)

( * ) Notice: Subject to any disclaimer, the term of this patent is extended or adjusted under 35 U.S.C. 154(b) by 0 days.

(21) Appl. No.: 10/051,649

(22) Filed: Jan. 17, 2002

(65) Prior Publication Data

US 2002/0095079 A1 Jul. 18, 2002

Related U.S. Application Data

(63) Continuation-in-part of application No. 09/552,260, filed on Apr. 19, 2000, now Pat. No. 6,415,168.

(51) Int. Cl.[7] .................................................. A61B 5/04
(52) U.S. Cl. ........................ 600/378; 439/885; 439/909; 607/38
(58) Field of Search .......................... 600/378, 373–381; 607/37, 38, 115, 116, 119, 122; 439/138, 142, 144, 798, 885, 909

(56) References Cited

U.S. PATENT DOCUMENTS

| | | | |
|---|---|---|---|
| 2,767,383 A | 10/1956 | Killian et al. | |
| 3,372,367 A | 3/1968 | Concannon | |
| 3,824,529 A | 7/1974 | Dorrell | |
| 3,866,615 A | 2/1975 | Hewson | |
| 4,211,462 A | * 7/1980 | Wolfthal | ..................... 439/588 |
| 4,245,642 A | 1/1981 | Skubitz et al. | |
| 4,245,645 A | 1/1981 | Arseneault et al. | |
| 4,341,226 A | 7/1982 | Peters | |
| 4,379,462 A | 4/1983 | Borkan et al. | |
| 4,461,304 A | 7/1984 | Kuperstein | |
| 4,516,820 A | 5/1985 | Kuzma | |
| 4,632,484 A | 12/1986 | Sinclair | |
| 4,633,889 A | 1/1987 | Talalla et al. | |
| 4,676,258 A | 6/1987 | Inokuchi et al. | |
| 4,712,557 A | 12/1987 | Harris | |
| 4,744,371 A | 5/1988 | Harris | |
| 4,840,580 A | 6/1989 | Saell et al. | |
| 4,850,359 A | 7/1989 | Putz | |
| 4,869,255 A | 9/1989 | Putz | |
| 5,560,358 A | 10/1996 | Arnold et al. | |
| 5,902,236 A | 5/1999 | Iversen | |
| 6,162,101 A | * 12/2000 | Fischer et al. | .............. 439/729 |

* cited by examiner

Primary Examiner—Michael Peffley
(74) Attorney, Agent, or Firm—Jansson, Shupe & Munger, Ltd.

(57) ABSTRACT

An electrical connector for multi-contact medical electrodes with plural-contact tails, including a tail-receiving member having a tail-receiving void defining an internal surface and an array of electrical conductors, preferably spring-loaded ball plungers, positioned along the internal surface. A locking mechanism is positioned within the tail-receiving member and can be moved from an open position in which a tail received within the void can be removed from the void, to a locked position in which the locking mechanism prevents removal of the tail. Some preferred embodiments include the locking mechanism being positioned adjacent the void opposite the conductors and extending into the void when in the locked position; the locking mechanism being a cam shaft and cam arrangement which allows for locking by rotation of the cam shaft; and the plural contacts being sleeves with necked-in ends to allow non-destructive withdrawal of the tail in the unlocked position.

20 Claims, 10 Drawing Sheets

ELECTRICAL CONNECTOR FOR MULTI-CONTACT MEDICAL ELECTRODES

RELATED APPLICATIONS

This is a continuation-in-part of patent application Ser. No. 09/552,260, filed on Apr. 19, 2000 by the inventor named herein, now U.S. Pat. No. 6,415,168.

FIELD OF THE INVENTION

This invention is related generally to electrical connectors for medical use and, more particularly, to medical connectors for multi-contact medical electrodes for use in facilitating surgical procedures.

BACKGROUND OF THE INVENTION

A variety of multi-contact medical electrodes, including depth electrodes, subdural strip electrodes and grid electrodes, are placed in the human body for various purposes, such as brain-mapping in epilepsy treatment. The plurality of wires necessarily extending from such electrodes typically lead to a plural-contact tail, which is a linear dielectric member with a linear array of sleeve-like contacts spaced therealong. Such plural-contact tails of multi-contact medical electrodes have been electrically joined to other equipment, such as monitoring equipment, by means of connectors designed specifically to accommodate such tails.

Many different connectors have been developed to facilitate such plural-contact connection. Examples of such prior plural-contact medical connectors are those disclosed in the following United States patents: U.S. Pat. No. 4,850,359 (Putz), U.S. Pat. No. 4,869,255 (Putz), U.S. Pat. No. 4,744,371 (Harris), U.S. Pat. No. 5,560,358 (Arnold et al.), U.S. Pat. No. 5,902,236 (Iversen), U.S. Pat. No. 4,516,820 (Kuzma), U.S. Pat. No. 4,712,557 (Harris), U.S. Pat. No. 4,461,304 (Kuperstein), U.S. Pat. No. 4,379,462 (Borkan et al.), U.S. Pat. No. 4,633,889 (Talalla et al.) and U.S. Pat. No. 4,676,258 (Inokuchi et al.).

Certain medical connectors of the prior art have a number of shortcomings and problems. Some prior connectors generally require a number of manual steps to operate, even for the final step of causing simultaneous electrical connection of the plural contacts. One-handed connection and disconnection may not be readily possible. Some prior devices require multiple parts which add to their complexity of operation.

Simplicity in structure and operation is particularly important considering that connection and disconnection typically occurs in a surgical setting, in which a surgeon or other doctor must be giving great attention to many other factors. Complexity in parts and operational procedures is a significant shortcoming, one which is important by medical personnel involved.

Maintaining reliable and constant connection throughout the period of use is another important consideration. Connectors which tend to provide electrical contact which is variable, depending on factors such as the degree of tightening, can be problematic. Still another shortcoming of certain prior art connectors is the lack of a definitive indication that electrical connection has been accomplished and put into effect.

Another concern with certain medical connectors for multi-contact electrodes, particularly in situations involving seizure disorders, is that devices essential to proper electrical connections can too easily be destroyed by inadvertent motions. More specifically, the plural-contact tails of multi-contact electrodes can break, or their plural contacts become dislodged, when forceful inadvertent yanking or pulling motions occur, as can occur during seizures. This is not a simple problem, because destruction of a plural-contact tail may make it difficult or impossible for a physician or technician to ascertain the proper association of contact leads with in-body contacts, and this makes further reliable use difficult or impossible for the in-body electrode associated with the destroyed plural-contact tail.

In summary, there remains a number of problems and shortcomings in prior connectors for use with multi-contact medical electrodes.

OBJECTS OF THE INVENTION

It is an object of this invention to provide an improved connector for multi-contact medical electrodes overcoming some of the problems and shortcomings of the prior art.

Another object of this invention is to provide an improved multi-contact medical connector which is simple in structure and operation in order to facilitate operations, including during surgery.

Another object is to provide an improved multi-contact medical connector requiring fewer manual steps to accomplish and secure electrical connection.

Another object is to provide an improved multi-contact medical connector which provides for locking the components in position after connection.

Another object is to provide an improved multi-contact medical connector which gives highly reliable electrical connections with minimal effort.

Another object is to provide an improved multi-contact medical connector which gives a definitive indication of the completion of electrical connection.

Still another object of the invention is to provide an improved multi-contact medical connection which is less susceptible to destruction of key connection parts due to inadvertent yanking, as can occur by virtue of seizure disorders.

These and other objects of the invention will be apparent from the following descriptions and from the drawings.

SUMMARY OF THE INVENTION

This invention is an improved electrical connector for in-body multi-contact medical electrodes having linear-array plural-contact tails. The electrical connector is of the type having a tail-receiving member and means for connection of all contacts. The improved multi-contact medical connector of this invention includes a tail-receiving member having an elongate tail-receiving void which receives the tail. The void defines an internal surface along which an array of electrical conductors are positioned. The conductors are biased toward the void to facilitate electrical engagement with the plural contacts of the tail when the tail is inserted into the void. The connector further includes a lock positioned within the tail-receiving member and moveable between an unlocked position and a locked position wherein the lock engages the tail and prevents the tail from being removed from the tail-receiving member. In preferred embodiments, the lock is positioned adjacent to the void and opposite from the array of conductors and engages the tail within the void. The lock preferably forces the tail against the internal surface when the lock is in the locked position. At the same time, the lock forces the contacts into the conductors. When in the unlocked position the electrical conductors are just beyond center with respect to the plural contacts of the tail, thereby providing reliable electrical contact.

The lock preferably comprises a rod and cams, the cams preferably being positioned in alignment with the conductors. The rod is movable in the tail-receiving member between unlocked and locked positions so that in the unlocked position the cams do not extend into the void and in the locked position the plunger forces the cams to extend into the void and force the contacts against the conductors. It is most preferable that the cam shaft is rotatable between the unlocked and locked positions so that in the unlocked position the cams do not extend into the void and in the locked position the cams extend into the void and force the contacts against the conductors.

A highly preferred embodiment of the invention includes a knob connected to the cam shaft to facilitate one-handed rotation of the cam shaft.

It is also preferred that the plural contacts of the tail are annular sleeves having necked-in ends, thereby allowing quick withdrawal of the plural-contact tail from the connector when in the unlocked position.

The tail-receiving member preferably has proximal and distal ends and the void extends from an opening at the proximal end to a stop near the distal end.

In a highly preferred embodiment, the electrical conductors are spring-loaded ball plungers. In such an embodiment the tail-receiving member defines wells along the internal surface holding the spring-loaded ball plungers and the ball plungers protrude beyond the internal surface into the internal space in the unlocked position.

The preferred method of securing connection between the medical electrode plural-contact tail and the tail-receiving member comprises: providing an array of electrical conductors positioned along the internal surface of the void in the tail-receiving member; providing a lock positioned adjacent to the void; inserting the tail into the void so that the contacts on the tail are aligned with the conductors; and moving the lock from an unlocked position to a locked position wherein the lock forces the tail against the internal surface to ensure that the tail cannot be withdrawn from the tail-receiving member. It is preferred that the conductors are biased toward the void to facilitate electrical engagement with the plural contacts of the tail.

In a highly preferred method, the lock comprises a rod and cams, and the cams are positioned in alignment with the conductors. To lock the tail inside the tail-receiving member, the rod is rotated so that the cams extend into the void and force the contacts against the conductors.

In alternate embodiment the improved multi-contact medical connector of this invention includes first and second elongate members which are pivotable with respect to one another about a pivot axis extending along their lengths. The first elongate member has a first face and an array of electrical conductors positioned therealong in an array which matches the spacing of the plural contacts of the plural-contact tail of the medical electrode with which the connector is used. The second elongate member extends along the first elongate member and has a tail-receiving void, a second face which is parallel to the void, and access openings along the second face to expose the plural tail contacts at the second face. The second elongate member is pivotable between open and closed positions with respect to the first elongate member. The pivoting is about an axis which extends along the common lengths of the elongate members. The closed position serves to place the plural contacts of a plural-contact medical electrode tail into engagement with the electrical conductors.

In a preferred embodiment of the alternate embodiment, a lock is positioned in one of the elongate members, most preferably the second elongate member, and is moveable between an unlocked position and a locked position wherein the lock engages the tail and prevents the tail from being removed from the tail-receiving void. In preferred embodiments, the lock is positioned adjacent to the void and opposite from the array of conductors when in the closed position and engages the tail within the void. The lock forces the contacts against the conductors. When in the closed and unlocked position the electrical conductors are just beyond center with respect to the plural contacts of the tail, thereby providing reliable electrical contact.

In highly preferred alternate embodiments, the second face is movable upon pivoting between the open position at which the second face is away from the first face and the closed position at which the second face is juxtaposed to the first face, and the electrical conductors are spring-loaded ball plungers along the first face which are biased toward the second face to facilitate electrical engagement with the plural contacts of the tail. The first elongate member preferably defines cylindrical wells (or "channels") along the first face which receive and hold the spring-loaded ball plungers. Such channels are preferably perpendicular to the first face. The distal ends of the ball plungers are held near the first face in positions for biased engagement against the contacts of the multi-contact tail when the first and second faces are in juxtaposition to one another.

In certain preferred alternate embodiments, the second elongate member has proximal and distal ends and the void extends from an opening at the proximal end to a stop near the distal end, and the first elongate member includes a pair of opposed inwardly-facing endwalls between which the second elongate member extends in nested fashion with its ends adjacent to the endwalls. The proximal end of the second elongate member is that end into which the multi-contact medical electrode tail is inserted, and the distal end is the opposite end.

In certain of such preferred alternate embodiments, one of the endwalls forms a cutaway portion through which the electrode tail passes, thereby allowing pivoting movement of the second elongate member without interference with the electrode tail. Preferably, the pivot axis extends through both endwalls and both ends and at least one pivot pin extends along a portion of the pivot axis between at least one of the endwalls and the end adjacent thereto. Two pivot pins along such axis are preferably used—one spanning between combination of endwall and end.

In preferred alternate embodiments, the first and second elongate members have first and second stop surfaces, respectively, which abut one another to define the closed position, and at the closed position the second elongate member positions the electrode tail such that the spring-loaded ball plungers are just beyond center (overcenter) with respect to the plural contacts of the tail. This configuration serves to provide reliable electrical contact and also helps to keep the connector in the closed position.

In certain preferred alternate embodiments, the second elongate member includes a grip flange which serves to facilitate pivoting of the second elongate member from the closed to the open position. Such grip flange extends away from the pivot axis and provides a thumb-grip surface.

In certain highly preferred alternate embodiments, the ball plungers protrude beyond the first face toward the second elongate member, and the access openings on the second face are designed to facilitate the closing action during which the plural contacts of the medical electrode tail are brought into engagement with the ball plungers. More specifically, the second face has a lead edge which is adjacent to the second stop surface when the second elongate member is in the closed position, and the access openings on the second face extend laterally to the lead edge such that the second elongate member has lateral openings receiving the ball plungers as the second elongate member is pivoted to the closed position.

The alternate medical connector of this invention has significant advantages over connectors of the prior art. The connector is compact, at least in part from the fact that the orientation of the pivot axis, which is along the length of the first and second elongate members, minimizes the space in which opening and closing movement occurs. The medical connector of this invention is also very easy to use in that it can be opened and closed with one hand. The connector also provides excellent electrical connections and provides definite open and closed positions to facilitate operation and understanding.

The invention includes the medical connectors as described above, and also includes the combination of such connectors with the linear-array plural-contact tails of a multi-contact medical electrode. In highly preferred embodiments, the plural contacts of the plural-contact tail are annular sleeves having necked-in (e.g., crimped) ends. This configuration of plural-contact tail with the medical connectors of this invention with spring-loaded ball plungers allows quick withdrawal of the plural-contact tail without destruction of the plural-contact tail. A sudden pull allows the plural-contact tail to pull out from the connector while the connector is in its closed, but not locked, position. This is brought about by the combination of spring-loaded ball plungers and the necked-in annular-sleeve contacts. The contacts will ride right over the line of ball plungers without causing destruction of the plural-contact tail.

This advantage is significant in that it minimizes or prevents the problems which can occur if a patient's seizure causes violent jerking and yanking movements during e.g., a brain-mapping session. Such activity can result in the need for an expensive and time-consuming reorganization and reassembly of electrical components in order to allow resumption of the intended medical activity.

BRIEF DESCRIPTION OF THE DRAWINGS

The drawings illustrate a preferred embodiment including the above-noted characteristics and features of the invention. The invention will be readily understood from the descriptions and drawings. In the drawings.

DETAILED DESCRIPTION OF PREFERRED EMBODIMENTS

FIGS. 1–6 illustrate an improved electrical connector 10 for use with an in-body multi-contact medical electrode (the in-body portion of which is not shown) having a linear-array plural-contact tail 12, having a linear array of electrical contacts 14 spaced therealong, each electrically linked by a tiny conductive wire running up and beyond tail 12 to a particular in-body contact on the in-body portion of the electrode. Connector 10 includes first and second elongate members 16 and 18 which are pivotable with respect to one another about a pivot axis A which extends along their lengths.

First elongate member 16 has a first face and an array of spring-loaded ball plungers 22 positioned therealong in a linear array which matches in its spacing the linear array of electrical contacts 14 of plural-contact tail 12. Second elongate member 18 extends along first elongate member 16 and has a linear tail-receiving void 24, a second face 26 which is parallel with and closely adjacent to void 24, and access openings 28 along second face 26 and intersecting void 24 to expose contacts 14 at second face 26 in positions of alignment with, and intersecting, the round distal ends 22a of spring-loaded ball plungers 22.

Figure 1:
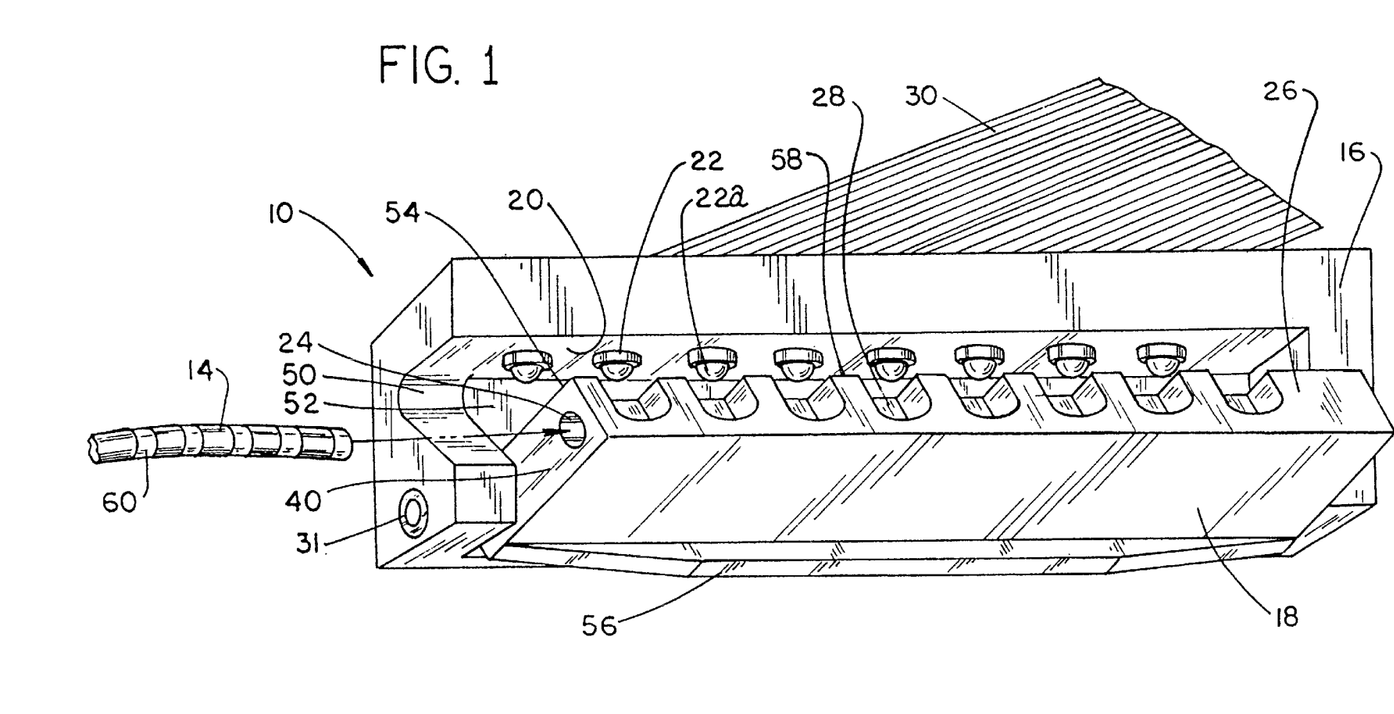
FIG. 1 is a perspective view of the alternate connector in an open condition, with the plural-contact tail of an in-body medical electrode in position for insertion into the connector.
Figure 2:
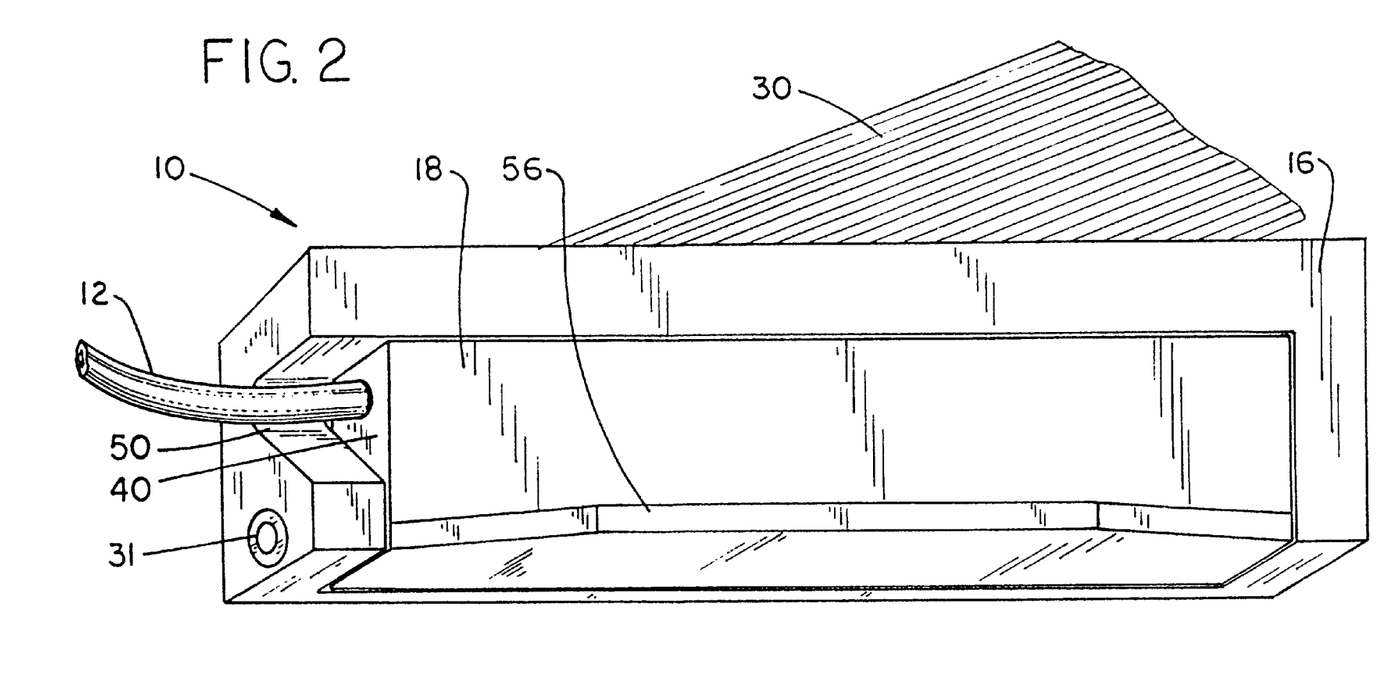
FIG. 2 is a perspective view as in FIG. 1, but with the connector in closed condition.
Figure 3:
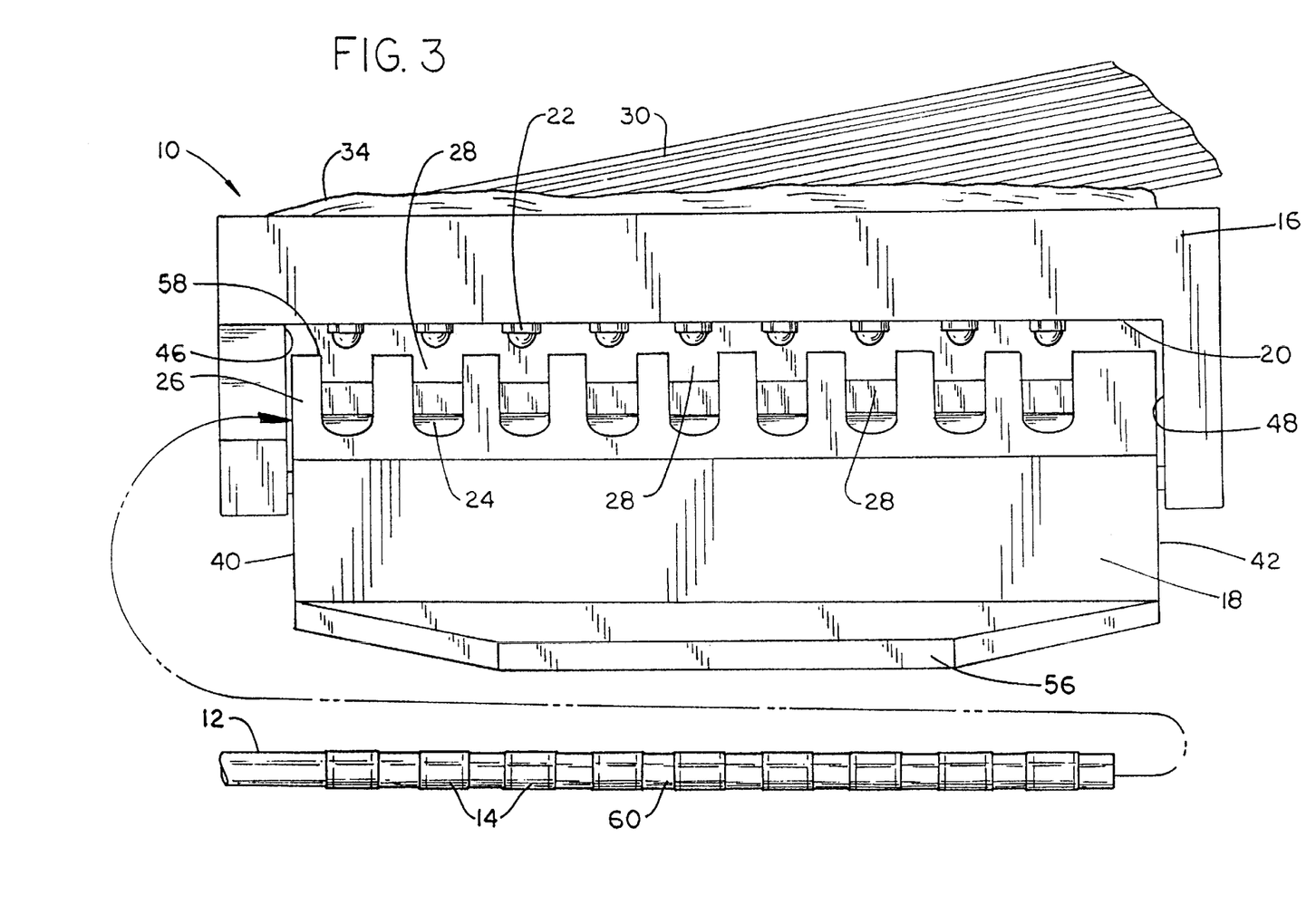
FIG. 3 is a front elevation of FIG. 1.
Figure 4:
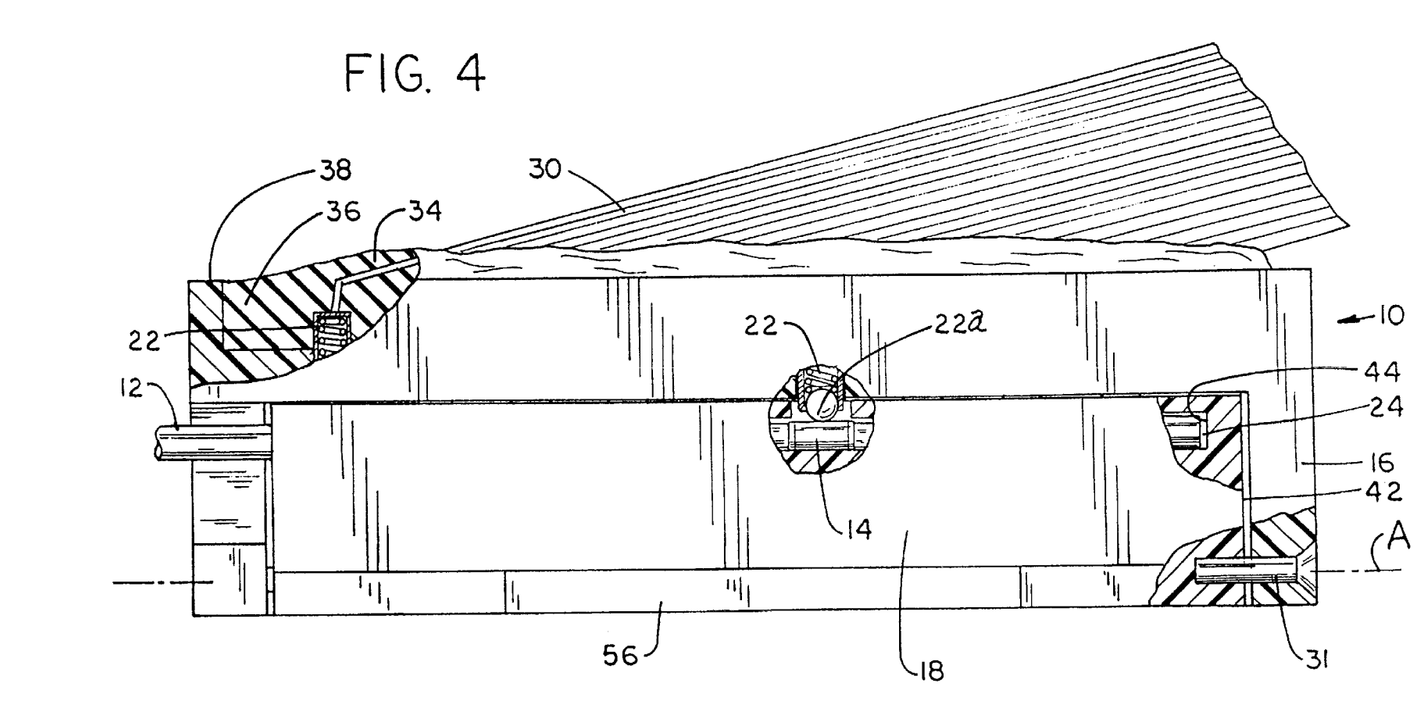
FIG. 4 is a front elevation of FIG. 2, but with cutaway portions to illustrate certain internal details.
Figure 5:
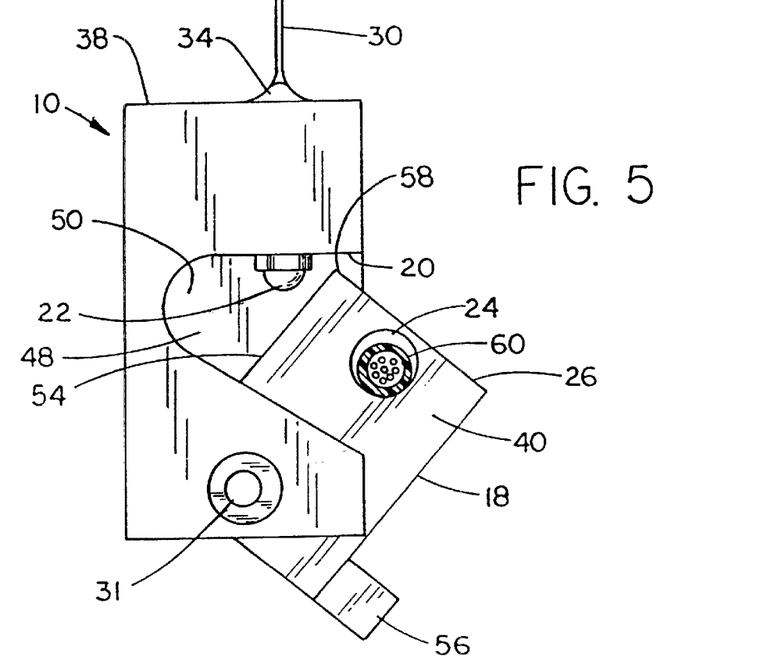
FIG. 5 is a left side elevation of the alternate connector, with the tail in section, showing the connector just before it is closed.
Figure 6:
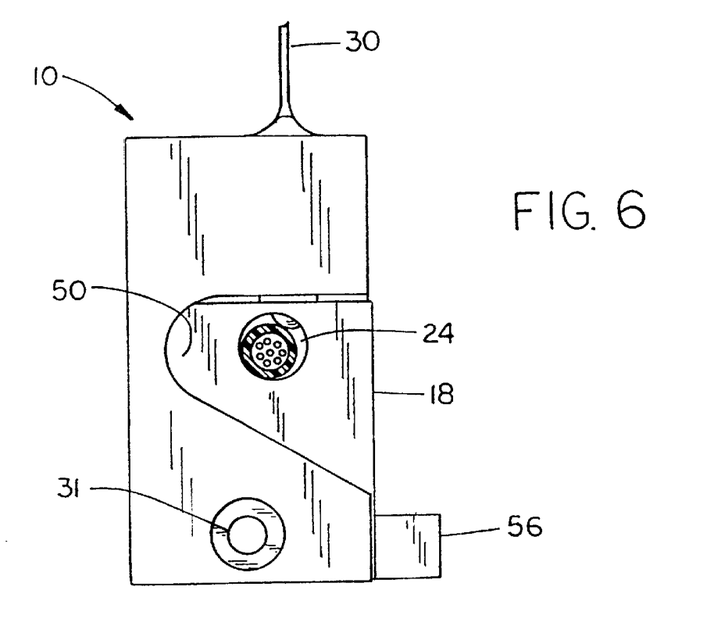
FIG. 6 is a left side elevation as in FIG. 5, but with the connector fully closed.

Second elongate member 18 pivots with respect to first elongate member 16 between open positions illustrated by FIGS. 1, 3 and 5 and a closed position illustrated by FIGS. 2, 4 and 6. Pivot pins 31 (see cutaway portion of FIG. 4) extend along axis A and pivotably connect second elongate member 18 with first elongate member 16. In the closed position, second face 26 is closely adjacent juxtaposed) to first face 18, such that contacts 14 are placed into engagement with spring-loaded ball plungers 22, each of which is electrically connected to one of the wires 30 which extend from connector 10 for easy connection by means not shown with other equipment.

First elongate member 16 preferably defines wells (or "channels") 32 along first face 20 which receive and hold spring-loaded ball plungers 22. Channels 32 are perpendicular to first face 20 and extend through first elongate member 16 to allow electrical connection with wires 30. Spring-loaded ball plungers 22 are potted in their positions in channels 32 and protruding just beyond first face 20 by an epoxy 34 applied in a recess 36 (see cutaway portion of FIG. 4) which is formed in the outer surface 38 of first elongate member 16. Distal ends 22a of spring-loaded ball plungers 22 are biased toward second face 26 to facilitate electrical engagement with contacts 14 of tail 12.

Second elongate member 18 has proximal and distal ends 40 and 42, and linear void 24 extends from an opening at proximal end 40 to a stop 44 near distal end 42. The position of stop 44 is fixed such that full insertion of tail 12 into void 24 causes contacts 14 to be in alignment with access openings 28 along second face 26 of second elongate member 18. First elongate member 16 includes a pair of opposed inwardly-facing endwalls 46 and 48 between which second elongate member 18 extends in nested fashion, with ends 40 and 42 adjacent to endwalls 46 and 48, respectively. As shown best in FIGS. 5 and 6, endwall 46, which is adjacent to proximal end 40 of second elongate member 18, is formed with a cutaway portion 50 to accommodate the presence of electrode tail 12 during pivoting movement of second elongate member 18.

As shown best in FIGS. 5 and 6, first and second elongate members 16 and 18 have first and second stop surfaces 52 and 54, respectively, which abut one another to define the closed position. As seen best in FIG. 6, at the closed position second elongate member 18 positions tail 12 such that spring-loaded ball plungers 22 are just beyond-center with respect to contacts 14 of tail 12.

Second elongate member 18 includes an integrally-formed grip flange 56 (see FIGS. 5 and 6), which extends away from pivot axis A. To open connector 10, downward thumb pressure is applied on grip flange 56 to pivot second elongate member 18 away from the closed position shown in FIG. 6.

As shown best in FIG. 3, second face 26 has a lead edge 58 which is adjacent to second stop surface 54 (and to first stop surface 52) when second elongate member 18 is in the closed position. Access openings 28 on second face 26 extend laterally on second face 26 to lead edge 58. This provides a lateral opening to each access openings 28 to receive spring-loaded ball plungers 22 as second elongate member 18 is pivoted to the closed position.

Figure 7:
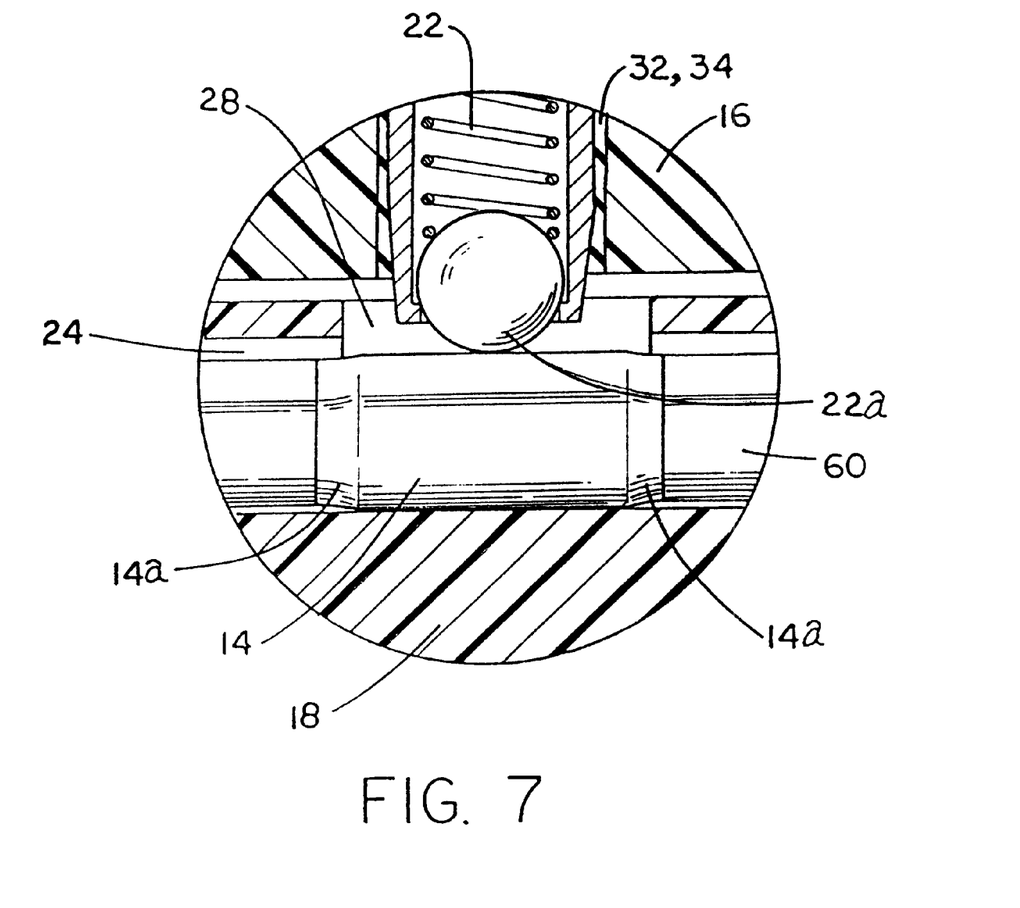
FIG. 7 is an enlarged fragmentary cutaway view of a portion of FIG. 4, as indicated in FIG. 4.

FIG. 7 illustrates details of contacts 12 and their relationship to distal ends 22a of spring-loaded ball plungers 22. Each contact 14 of plural-contact tail 12 is an annular sleeve which includes necked-in ends 14a, formed by crimping. As can be seen, the outer diameter of contact sleeves 14 are slightly greater than the outer diameter of the adjacent dielectric support tube 60 along which contacts 14 are mounted. As earlier noted, this allows quick removal of plural-contact tail 12 from medical connector 10, inadvertent or otherwise, without causing destruction of plural-contact tail 12.

First and second elongate members 16 and 18 of medical connector 10 may be made of hard plastic materials, a wide choice of which is available and will be apparent to those receiving this disclosure. Second elongate member 18 is preferably made of translucent or transparent material so that the positions of contacts 14 can be seen even without looking at access openings 28. A wide variety of materials is available for the various parts discussed and illustrated herein.

Figure 8:
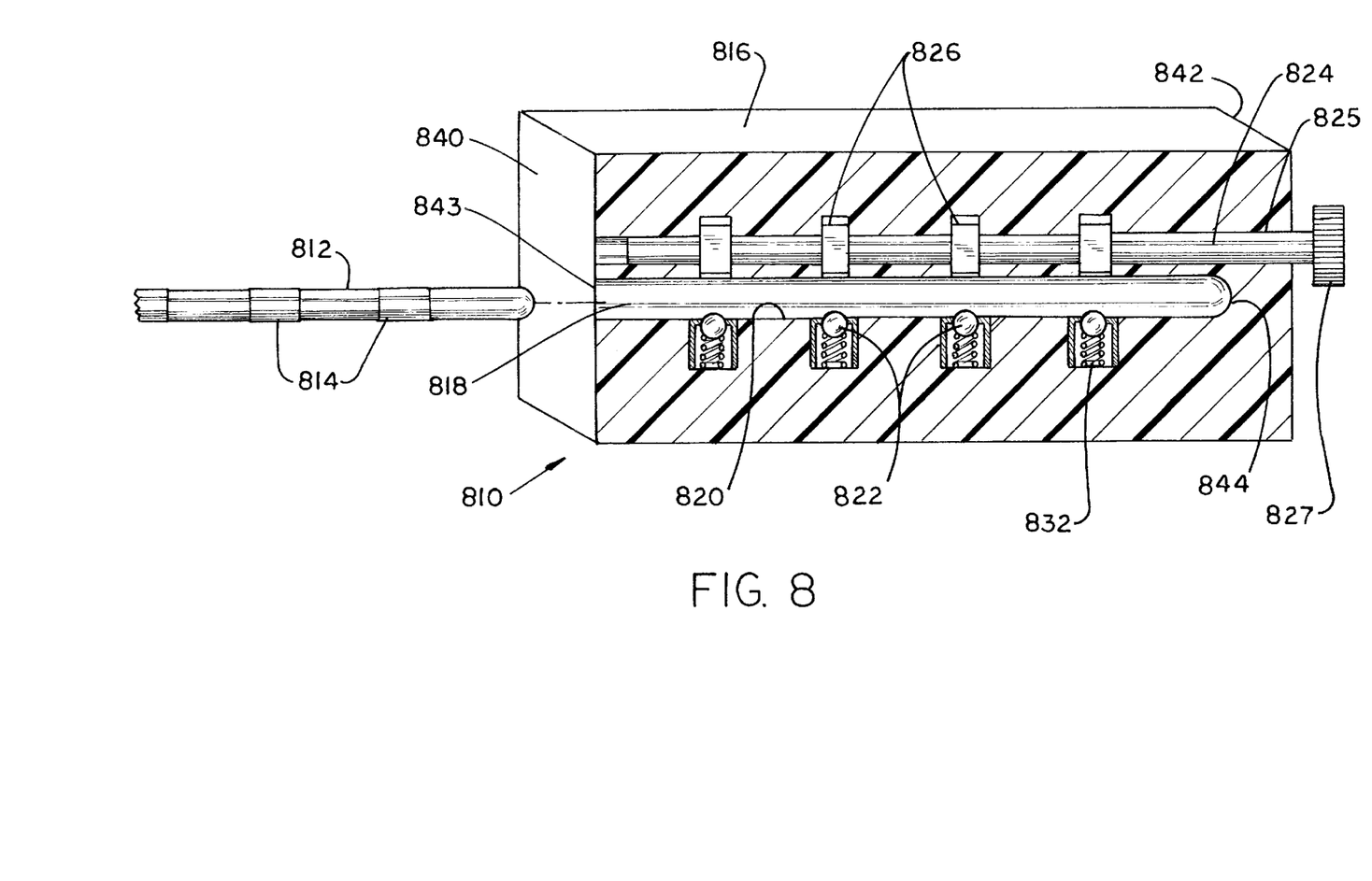
FIG. 8 is a perspective view of a cross section of the preferred electrical connector and tail.

FIG. 8 shows a cross-section view of the preferred connector and plural-contact tail. Connector or tail-receiving member 816 includes tail-receiving void 818 into which tail 812 may be inserted. Void 818 defines internal surface 820. Positioned along internal surface 820 are conductors 822. Conductors 822 are preferably spring-loaded ball plungers which extend and are biased into void 818. Void 818 extends from proximal opening 843 to distal stop 844.

Connector 816 further includes lock 825 which is comprised of cams 826 and cam shaft or rod 824. Lock 825 is positioned parallel to and adjacent void 818, opposite conductors 822. As shown, lock 825 is in the unlocked position in which cams 826 do not extend into void 818. Upon rotation of shaft 824, preferably via knob 827, cams 826 extend into void 818.

Tail 812 includes electrical contacts 814 which are preferably sleeves with necked in ends to allow non-destructive withdrawal of tail 812 when tail-receiving member 816 is in the unlocked position. Contacts 814 are spaced along tail 812 in a corresponding manner to the orientation of conductors 822 spaced along internal surface 820.

Figure 9:
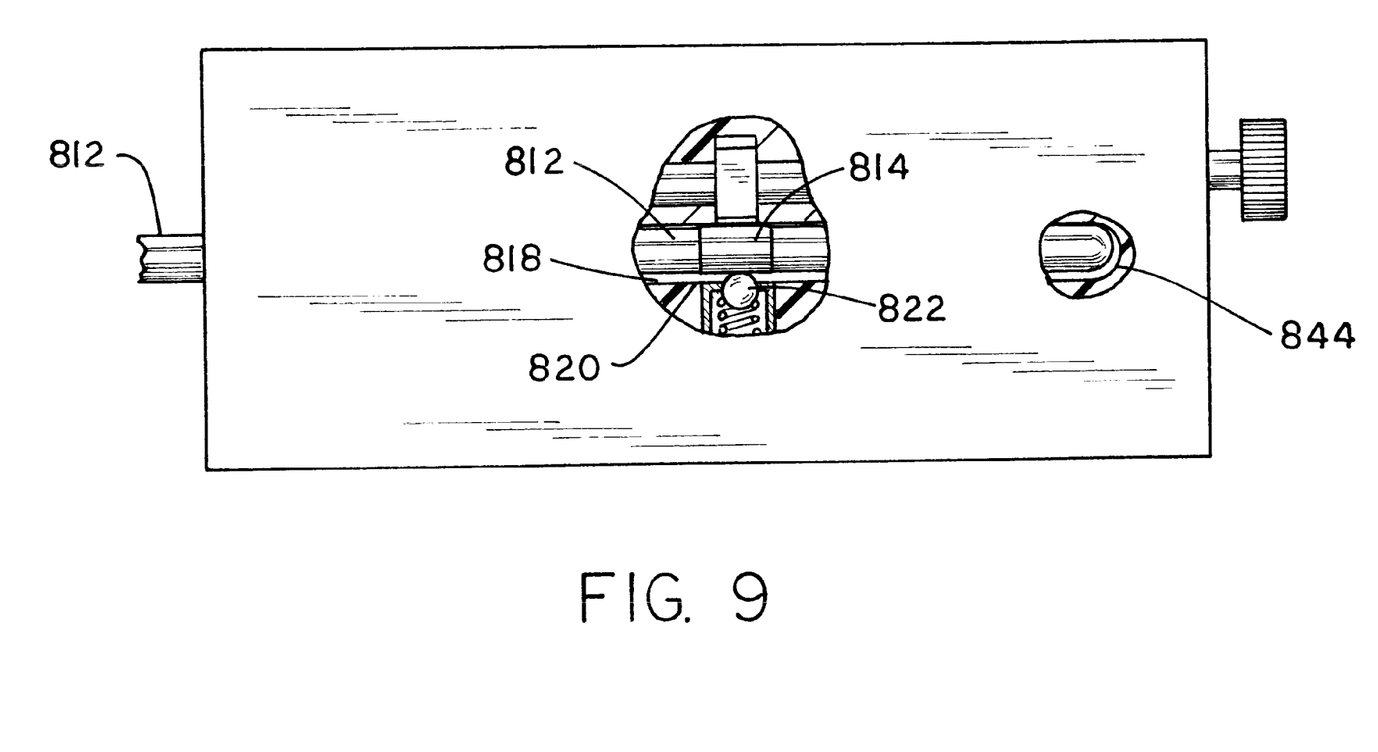
FIG. 9 is a perspective view of the preferred electrical connector receiving a tail, but with cutaway portions to illustrate internal details.

FIG. 9 shows the preferred electrical connector and tail in connection but unlocked. Tail 812 is inserted into void 818 until its distal end reaches stop 844. At this point contacts 814 are aligned with conductors 822. Conductors 822 extend into void 818 and ensure reliable connection with contacts 814. [Tial] Tail 812 is typically forced away from the portion of internal surface 820 on which conductors 822 are positioned.

Figure 10:
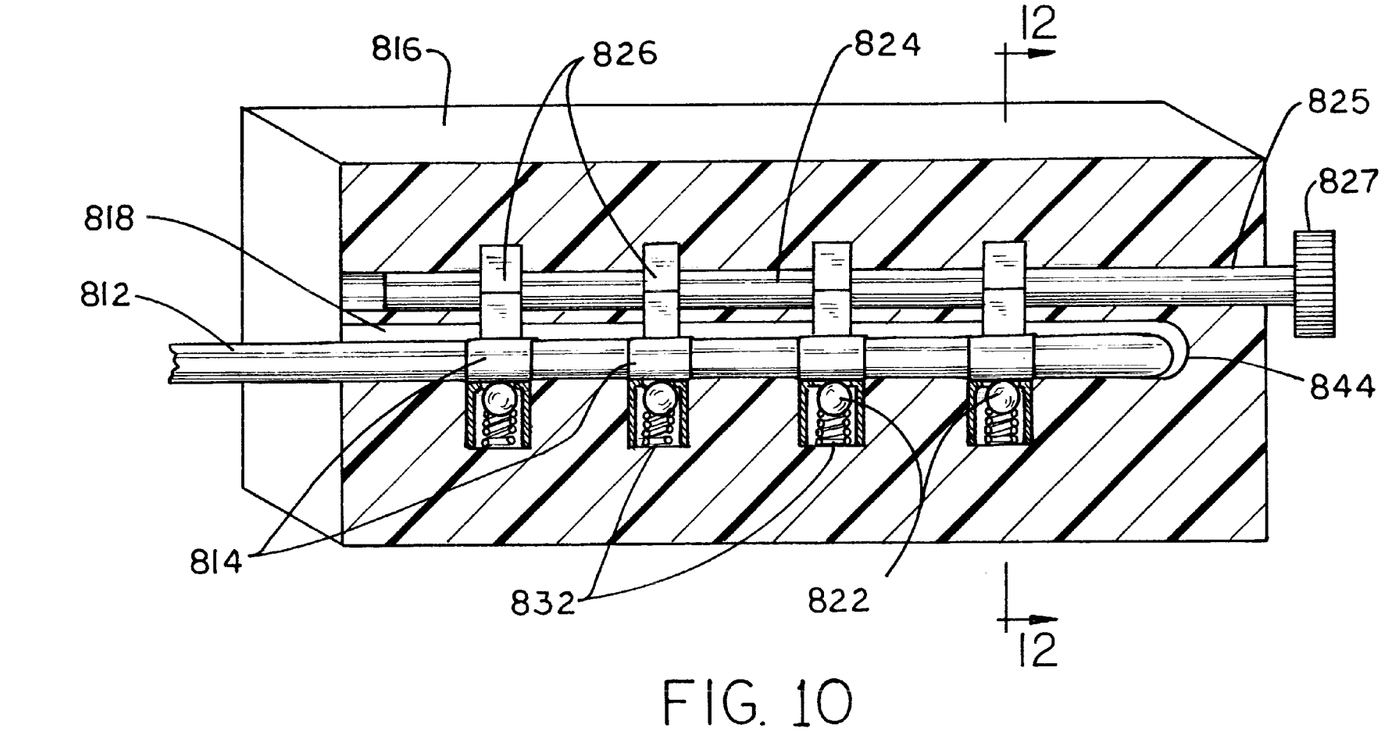
FIG. 10 is a perspective view of a cross section of the preferred electrical connector and tail

FIG. 10, the connector is locked to prevent removal of tail 812 from void 818. As can be seen, in the locked position cams 826 extend into void 818 from the side of internal surface 820 opposite conductors 822. Cams 826 are extended into void 818 by the rotation of cam shaft 824, preferably by a rotation of 45 degrees. Cams 826 force contacts 818 against conductors 822. [Conductors 822. Conductors] such that conductors 822 are pushed into wells 832 which creates an increasing spring force against contacts 814. Cams 826 force tail 812 against the portion of internal surface 820 along which conductors 822 are positioned. In this manner the counteracting forces of cams 826 and conductors 822 ensure reliable connection and prevent removal of tail 812 from void 818.

Figure 11:
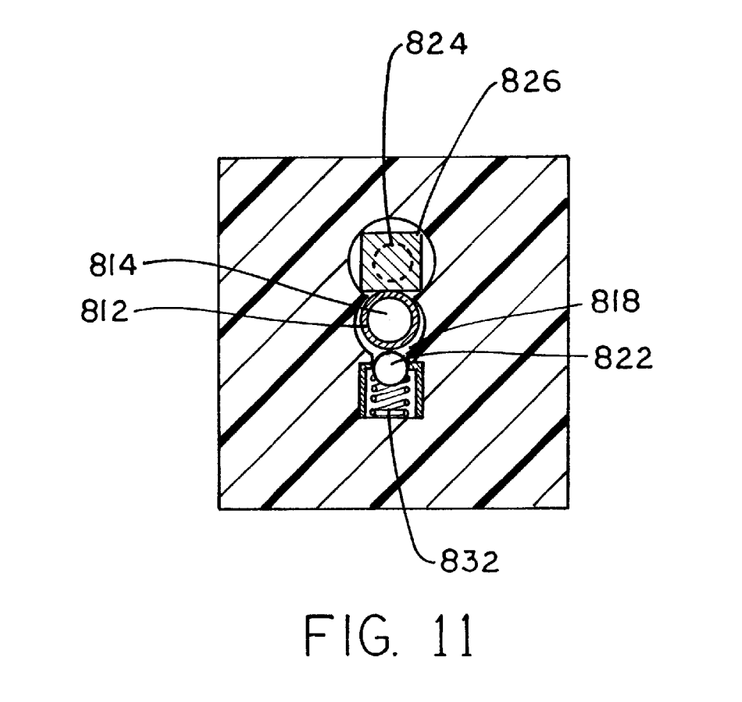
FIG. 11 is a cross section view taken along the direction of tail insertion showing the connection of the preferred contact and conductor in the unlocked position.
Figure 12:
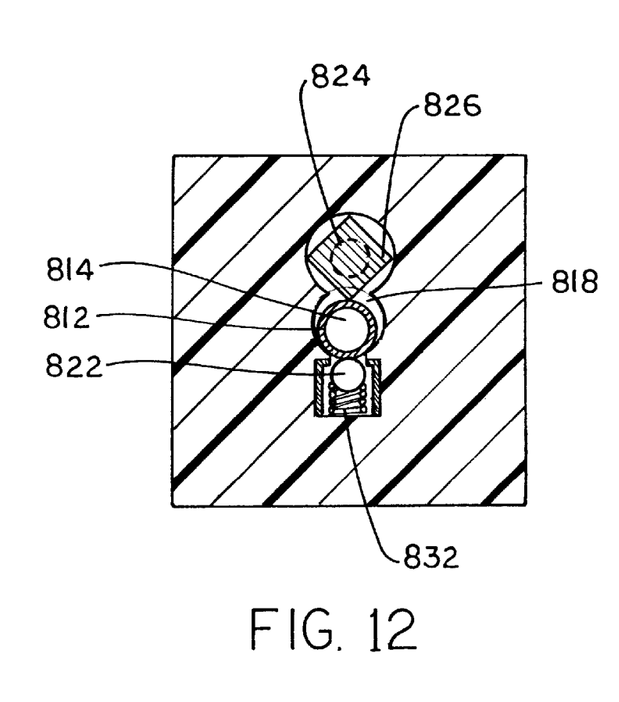
FIG. 12 is a cross section view taken along the direction of tail insertion showing the connection of the preferred contact and conductor in the locked position

FIGS. 11–12 show the cross section view of the connection of a conductor and contact in unlocked and locked configurations respectively. Contact 814 is shown as a sleeve circling tail 812. Contact 814 is aligned and in contact with conductor 822 which extends into tail-receiving void 818. Cam shaft 824 is positioned adjacent void 818 opposite from conductor 822. Cam 822 is connected to cam shaft 824 so that rotation of cam shaft 824 caused cam 822 to enter void 818. In FIG. 12 cam shaft 824 has been rotated 45 degrees from its position in FIG. 11 so that cam 824 enters void 818 and contacts tail 812 or contact 814. Recess 828 surrounds cam 826 so that cam may be rotated within tail-receiving member.

When cam 826 extends into void 818 it causes tail 812 to be forced toward internal surface 820 adjacent conductor 222. Tail 812 may contact internal surface 820 while conductor 822 is forced from well 832 into contact with contact 814 by spring force. In this manner tail 812 is locked into position within void 818.

Tail-receiving member 816 may be made of hard plastic materials, a wide choice of which is available and will be apparent to those receiving this disclosure. One face of tail-receiving member may be made of translucent or transparent material so that the positions of contacts 814 can be seen within member 816. A wide variety of materials is available for the various parts discussed and illustrated herein.

While the principles of this invention have been described in connection with specific embodiments, it should be understood clearly that these descriptions are made only by way of example and are not intended to limit the scope of the invention.

What is claimed is:

1. In an electrical connector for in-body multi-contact medical electrodes with linear-array plural-contact tails, having a tail-receiving member and means for connection of all contacts, the improvement comprising:

the tail-receiving member having an elongate void for receiving the tail, the void defining an internal surface;

a locked position within the tail-receiving member and moveable between an unlocked position and a locked position wherein the lock engages the tail and prevents the tail from being removed from the tail-receiving member, and an array of electrical conductors positioned along the internal surface, the conductors being biased toward the void to facilitate electrical engagement with the plural contacts of the tail, the conductors being positioned opposite the lock such that the tail is compressed between the conductors and the lock when the lock is in the locked position.

2. The multi-contact medical connector of claim 1 wherein the lock engages the tail within the void.

3. The multi-contact medical connector of claim 1 wherein the lock is positioned within the tail-receiving member adjacent to the void.

4. The multi-contact medical connector of claim 1 wherein the lock forces the tail against the internal surface when the lock is in the locked position.

5. The multi-contact medical connector of claim 1 wherein the plural contacts of the tail are annular sleeves having necked-in ends, thereby allowing quick withdrawal of the plural-contact tail from the connector when in the unlocked position.

6. The multi-contact medical connector of claim 1 wherein the tail-receiving member has proximal and distal ends and the void extends from an opening at the proximal end to a stop near the distal end.

7. The multi-contact medical connector of claim 1 wherein at the unlocked position the electrical conductors are just beyond center with respect to the plural contacts of the tail, thereby providing reliable electrical contact.

8. The multi-contact medical connector of claim 1 wherein the lock comprises a rod and cams, the cams being positioned in alignment with the conductors, whereby the rod is movable in the tail-receiving member between the unlocked and locked positions so that in the unlocked position the cams do not extend into the void and in the locked position the rod forces the cams to extend into the void to force the contacts against the conductors.

9. The multi-contact medical connector of claim 1 wherein the lock comprises a cam shaft and cams, the cams being positioned in alignment with the conductors, whereby the cam shaft is rotatable between the unlocked and locked positions so that in the unlocked position the cams do not extend into the void and in the locked position the cams extend into the void and force the contacts against the conductors.

10. The multi-contact medical connector of claim 9 wherein a knob is connected to the cam shaft to facilitate one-handed rotation of the cam shaft.

11. In an electrical connector for in-body multi-contact medical electrodes with linear-array plural-contact tails, having a tail-receiving member and means for connection of all contacts, the improvement comprising:

the tail-receiving member having an elongate void for receiving the tail, the void defining an internal surface;

an array of electrical conductors positioned along the internal surface, the electrical conductors being spring-loaded ball plungers which are biased toward the void to facilitate electrical engagement with the plural contacts of the tail; and a lock positioned within the tail-receiving member and moveable between an unlocked position and a locked position wherein the lock engages the tail and prevents the tail from being removed from the tail-receiving member.

12. The multi-contact medical connector of claim 11 wherein the tail-receiving member defines wells along the internal surface holding the spring-loaded ball plungers.

13. The multi-contact medical connector of claim 11 wherein the ball plungers protrude beyond the internal surface into the internal space in the unlocked position.

14. An electrical connector for connecting to an in-body multi-contact medical electrode with a tail having axially-spaced contacts, the connector comprising:

a tail-receiving member having an elongate axially-extending void for receiving the tail, the void defining an internal surface;

a plurality of electrical conductors axially-spaced along the internal surface such that the conductors are aligned with the axially-spaced contacts when the tail is received within the void, the conductors being biased toward the void to facilitate electrical engagement with the axially-spaced contacts of the tail, and a lock positioned within the tail-receiving member and moveable between an unlocked position and a locked position wherein the lock engages the tail and prevents the tail from being removed from the tail-receiving member.

15. The electrical connector of claim 14 wherein the conductors are positioned opposite the lock such that the tail is compressed between the conductors and the lock when the lock is in the locked position.

16. The electrical connector of claim 14 wherein the lock is positioned within the tail-receiving member adjacent to the void.

17. The electrical connector of claim 14 wherein the lock comprises a cam shaft and cams, the cams being positioned in alignment with the conductors, whereby the cam shaft is rotatable between the unlocked and locked positions so that in the unlocked position the cams do not extend into the void and in the locked position the cams extend into the void and force the contacts against the conductors.

18. The electrical connector of claim 14 wherein the electrical conductors are spring-loaded.

19. The electrical connector of claim 14 wherein the plurality of electrical conductors are fixed in position along the internal surface before insertion of the tail.

20. The electrical connector of claim 14 wherein the lock is moveable from the locked position to the unlocked position to allow the tail to be removed from the tail-receiving member and moveable from the unlocked position to the locked position to prevent the tail from being removed from the tail-receiving member.

* * * * *

UNITED STATES PATENT AND TRADEMARK OFFICE
CERTIFICATE OF CORRECTION

PATENT NO. : 6,671,534 B2
APPLICATION NO. : 10/051649
DATED : December 30, 2003
INVENTOR(S) : Putz It is certified that error appears in the above-identified patent and that said Letters Patent is hereby corrected as shown below:

In column 8, line 66, delete "locked position" and insert --lock positioned-- in place thereof.

Signed and Sealed this

Thirtieth Day of January, 2007

JON W. DUDAS
*Director of the United States Patent and Trademark Office*